(12) United States Patent
Qian et al.

(10) Patent No.: US 9,171,128 B2
(45) Date of Patent: Oct. 27, 2015

(54) SYSTEM AND METHODS FOR QUANTITATIVE IMAGE ANALYSIS PLATFORM OVER THE INTERNET FOR CLINICAL TRIALS

(75) Inventors: Jian-Zhong Qian, Princeton Junction, NJ (US); Xiaolan Zeng, Princeton, NJ (US); Guo-Qing Wei, Plainsboro, NJ (US); Li Fan, Belle Mead, NJ (US)

(73) Assignees: EDDA TECHNOLOGY, INC., Princeton, NJ (US); EDDA TECHNOLOGY (SUZHOU) LTD., Suzhou (CN)

(*) Notice: Subject to any disclaimer, the term of this patent is extended or adjusted under 35 U.S.C. 154(b) by 664 days.

(21) Appl. No.: 13/345,841

(22) Filed: Jan. 9, 2012

(65) Prior Publication Data
US 2012/0207361 A1 Aug. 16, 2012

Related U.S. Application Data

(60) Provisional application No. 61/430,802, filed on Jan. 7, 2011.

(51) Int. Cl.
*G06K 9/00* (2006.01)
*G06F 19/00* (2011.01)

(52) U.S. Cl.
CPC ............ *G06F 19/321* (2013.01); *G06F 19/363* (2013.01)

(58) Field of Classification Search
None
See application file for complete search history.

(56) References Cited

U.S. PATENT DOCUMENTS

| | | | |
|---|---|---|---|
| 6,272,469 B1 * | 8/2001 | Koritzinsky et al. ............. | 705/2 |
| 6,381,557 B1 * | 4/2002 | Babula et al. ................. | 702/183 |
| 6,494,831 B1 * | 12/2002 | Koritzinsky ................... | 600/301 |
| 6,574,304 B1 * | 6/2003 | Hsieh et al. ..................... | 378/62 |
| 6,687,329 B1 * | 2/2004 | Hsieh et al. ..................... | 378/62 |
| 6,785,410 B2 * | 8/2004 | Vining et al. ................. | 382/128 |
| 7,139,417 B2 | 11/2006 | Nicolas et al. | |
| 7,289,651 B2 * | 10/2007 | Vining et al. ................. | 382/128 |
| 8,201,192 B2 * | 6/2012 | Becker et al. ................. | 719/328 |
| 8,345,991 B2 * | 1/2013 | Gering et al. ................. | 382/232 |
| 2004/0052328 A1 * | 3/2004 | Sabol et al. ..................... | 378/37 |
| 2004/0068167 A1 * | 4/2004 | Hsieh et al. ................... | 600/407 |
| 2004/0147840 A1 * | 7/2004 | Duggirala et al. ............ | 600/437 |
| 2007/0055977 A1 * | 3/2007 | Becker et al. ................. | 719/330 |
| 2007/0061112 A1 | 3/2007 | Nagai et al. | |
| 2007/0276214 A1 * | 11/2007 | Dachille et al. ............... | 600/407 |
| 2008/0089596 A1 | 4/2008 | Choi et al. | |
| 2008/0109250 A1 | 5/2008 | Walker et al. | |
| 2008/0162229 A1 | 7/2008 | Moore et al. | |
| 2009/0164247 A1 * | 6/2009 | Dobler et al. ..................... | 705/3 |
| 2009/0297013 A1 * | 12/2009 | Chaudhuri ................... | 382/132 |
| 2010/0040212 A1 | 2/2010 | Sakai et al. | |
| 2013/0173308 A1 * | 7/2013 | Hough et al. ..................... | 705/3 |

OTHER PUBLICATIONS

International Search Report corresponding to PCT/US12/20593 dated May 10, 2012.

* cited by examiner

*Primary Examiner* — Jason Heidemann
(74) *Attorney, Agent, or Firm* — Pillsbury Winthrop Shaw Pittman LLP

(57) ABSTRACT

The present disclosure is directed at a system and method for analyzing clinical trial data over a network. The system and method specifics image protocols, encodes a number of protocols and communicates that information to an acquisition unit that appends the protocols to a digital image. When the image needs to be analyzed to gather clinical trial data, the encoded information is extracted and the correct software application is initialized and used to analyze the image.

21 Claims, 4 Drawing Sheets

SYSTEM AND METHODS FOR QUANTITATIVE IMAGE ANALYSIS PLATFORM OVER THE INTERNET FOR CLINICAL TRIALS

CROSS REFERENCE TO RELATED APPLICATIONS

This application claims priority from U.S. Provisional Application No. 61/430,802 filed Jan. 7, 2011 the disclosure of which is incorporated herein by reference in its entirety.

TECHNICAL FIELD

The present disclosure generally relates to system and methods for image analysis of clinical trials over a network. More specifically, the present disclosure relates to a system and method for quantitative image analysis for pharmaceutical clinical trials over the internet.

BACKGROUND

Recently quantitative imaging has become a very important topic for pharmaceutical companies. Drug development is very costly and lengthy in time and often different phases of clinical trials are necessary in order to validate the effectiveness of a drug. Presently, pharmaceutical companies are developing agents that, when injected into human subjects, can be imaged, at the functional and anatomical levels to quantify the effectiveness of a drug. This type of agent can significantly reduce the length of clinical trial and the cost of drug development.

Accordingly, medical image analysis vendors are developing dedicated systems and tools to analyze and quantify such clinical trial images. For different image modality, such as CT, MR, PET, SPECT, different dedicated analysis tools may need to be developed. Utilizing present methods, analysis is application-centered. That is, the interested user first starts the application and then loads the data that is intended for the application. The respective clinical trial center may therefore need to have installed multiple applications for different clinical trials. It is therefore inefficient for users to look for, and locate, the right application and load the right image intended for analysis. Furthermore, it is not uncommon that two analysis software applications from two different vendors can do the same analysis. However, the analysis results may differ due to variations in the vendor platforms. For example, some critical parameters, such as the CT Hounsfield unit value for thresholding, may be hard coded in each application and vary across platforms. There is presently, no standardized way to minimize these differences and their impact among analysis results.

It is therefore highly desirable to have a method to organize the applications in an image-centered way, so that images and applications can not be mismatched. Furthermore, it is also highly desirable to systematically reduce or eliminate the analysis result difference encountered by different vendors.

SUMMARY

In an embodiment of the present disclosure, a system for analyzing an image over a network is disclosed. The system comprises a trial specification unit, an encoding unit, an image acquisition unit, an application dispatch unit, an analysis unit, a user coordination unit, and an application result compensation generation unit.

In an embodiment, the analyzing is part of a clinical trial. In another embodiment, the images are medical diagnostic image. In still another embodiment, the encoding unit encodes information related to at least one of the following: a protocol description, an image type, an application type, an application parameter, and an analysis protocol.

In another embodiment, the encoded information is communicated to the image acquisition unit. In another embodiment, the encoded information is appended to a header of a Digital Imaging and Communication in Medicine (DICOM) image.

In still another embodiment the system includes a trial specification extraction unit, a trial specification interface unit, an application repository and a database for storing the DICOM images utilized. In the embodiment, the application dispatch unit may select an image from the database and the application dispatch unit further selects an application from the application repository to process the selected image. In another embodiment, the application generates results based on the analysis of the selected images and outputs them to the analysis unit.

In another embodiment, a method implemented on a machine having at least one processor, storage, and a communication platform connected to a network for analyzing clinical trial data is disclosed. The method comprises specifying image protocols, encoding a plurality of trial protocols, communicating the encoded trial protocols, via the network to an acquisition unit, acquiring, via the acquisition unit, a Digital Imaging and Communication in Medicine (DICOM) image and appending the encoded protocols to the DICOM images via the acquisition unit. The method further requires decoding the appended plurality of trial protocols, via a dispatch unit, identifying a trial protocol from the plurality of trial protocols, initializing a software application based on the identify of the trial protocol and performing an analysis of the DICOM image utilizing the software application.

In another embodiment, the analysis is used to generate compensation data to be used by the software application to refine results. In still a further embodiment, the compensation data is used to revise trial protocols. In another embodiment, the analysis is used to generate clinical trial data. In another embodiment, the plurality of trial protocols includes at least one of the following: a protocol description, an image type, an application type, an application parameter, and an analysis protocol.

In an embodiment, a machine-readable tangible and non-transitory medium, having information for analyzing clinical trial data, recorded thereon is disclosed. The machine-readable tangible and non-transitory medium comprises information, that when read by the machine, causes the machine to specify image protocols, encode a plurality of trial protocols, communicate the encoded trial protocols, via the network to an acquisition unit, acquire, via the acquisition unit, a Digital Imaging and Communication in Medicine (DICOM) image. It further causes the appending of the encoded protocols to the DICOM images via the acquisition unit, the decoding of the appended plurality of trial protocols, via the dispatch unit and identifying a trial protocol from the plurality of trial protocol. The medium further initializes a software application based on the identify of the trial protocol and performs an analysis of the DICOM image utilizing the software application.

In another embodiment, the medium contains information recorded thereon, for analysis used to generate a compensation data to be used by the software application. In another embodiment, the compensation data is used to revise the trial protocols. In still another embodiment, the analysis is used to generate clinical trial data. In a further embodiment, the plurality of trial protocols includes at least one of the following: a protocol description, an image type, an application type, an application parameter, and an analysis protocol.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

The present disclosure is directed to a system and method for a platform that can minimize the analysis result discrepancies among applications. The present disclosure is described in an Internet environment, however, it should be understood, that it may be deployed in any networking environment. For example, a network can be a local area network (LAN), a wide area network (WAN), a public network, a private network, a proprietary network, a Public Telephone Switched Network (PSTN), the Internet, a wireless network, a virtual network, or any combination thereof. A network may also include various network access points, e.g., wired or wireless access points such as base stations or Internet exchange points, through which a data source may connect to the network in order to transmit information via the network.

Furthermore, the present disclosure is described in the context of analyzing clinical trial images. It should be understood however, that the present disclosure is not limited to such an embodiment and may be utilized for other types of data analysis such as diagnosis data in a hospital environment.

Figure 1:
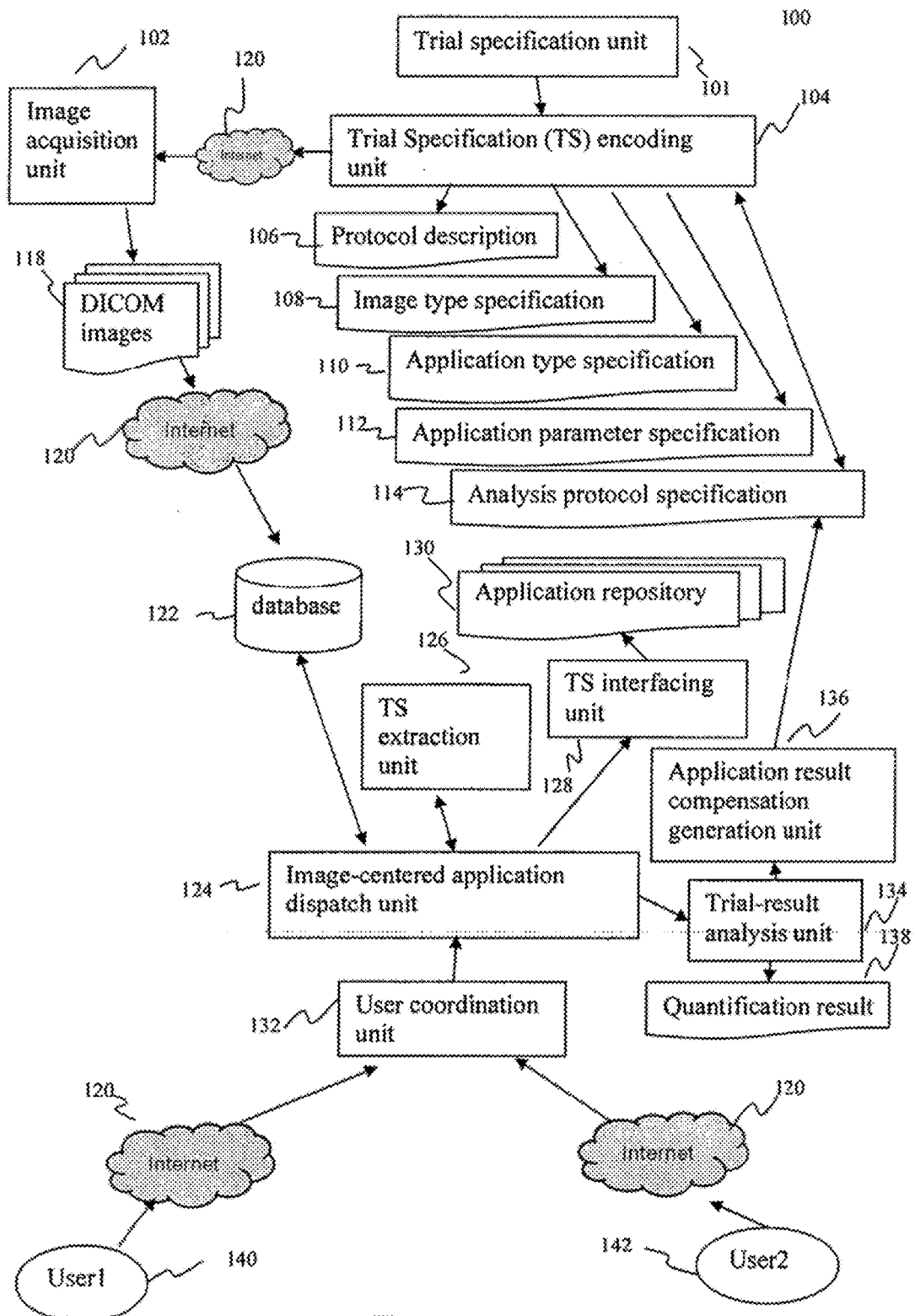
FIG. 1 is a system diagram for a new platform for quantitative image analysis in accordance with the present disclosure.

FIG. 1 shows a system diagram of an embodiment of a quantitative image analysis system 100 designed for analyzing clinical trial images. The system may consist of a Trial Specification (TS) unit 101, an image acquisition unit 102, a TS encoding unit 104, an image-centered application dispatch unit 124, a TS extraction unit 126, a TS interfacing unit 128, a user coordination unit 132, a trial-result analysis unit 134, and an application-result compensation generation unit 136.

The trial specification unit 101 specifies the trials. The TS encoding unit 104 encodes the specification in a pre-defined format. The content to be encoded includes, but is not limited to protocol description 106, image type specification 108, application type specification 110, application parameter specification 112, analysis protocol specification 114.

In an embodiment, the protocol description 106 may be a brief summary of the clinical trial protocol. The image type specification 108 defines what image modality and acquisition parameters may be used for the trial. The application specification 110 defines what type of analysis software shall be used for analyzing the images. The application parameter specification 112 specifies what parameters may need to be used in analyzing the images. Some critical parameters, such as threshold values, e.g., the percentage of drop from the highest isotope count in SPECT images for segmenting liver organ, may be specified. Other examples of critical parameters may include, but not limited to, image enhancement quantification criteria, such as rate of lesion enhancement over time, and the minimum remnant organ functional percentage allowed, etc.

The analysis protocol specification unit 114 specifies how the quantification results from an application shall be analyzed. For example, what kind of statistical methods may need to be used. It may also specify what kind of compensation may need to be applied to the analysis result when a specific application is used. This compensation amount may be generated from statistical analysis of prior use of an application. The coded TS output from the unit 104 may be input to the image acquisition unit 102 directly or over a network such as the internet 120. The image acquisition unit may be located with the TS encoding unit 104 or remotely from the TS encoding unit. The image acquisition unit 102 may load the TS parameters during the image acquisition process. For example, the acquisition parameters from TS may be used during the image acquisition process. Other parameters, such as the injection rate of a contrast agent may also be used to control the acquisition device. The image acquisition unit 102 also embeds the encoded TS parameters received from TS encoding unit 104 into the header of the DICOM (Digital Imaging and Communication in Medicine) images 118 that are generated by the acquisition device, which may be any type of medical imaging device, such as CT, MRI, SPECT or MRI.

A user 140 may access the image analysis software through a user coordination unit 132. Through the user coordination unit 132, the user 140 may specify whether the use-session will be a single user or a multiple user session. In the case of multiple users, one or more of the users may be able to see and control the same use-session. The image-centered application dispatch unit 124 opens an image from image database 122. The TS extraction unit 126 extracts the TS images from the DICOM header of the images. Through the extracted application type specification, the specified analysis software is selected from the application repository 130 and started. All software applications in the application repository 130 are required to implement a set of pre-defined interfaces that can accept pre-defined application parameters. Through the TS interfacing unit 128, the application parameters may be passed to the specified application. After the user 140 or 142 finishes the analysis, the quantitative analysis result may be analyzed by the trial-result analysis unit 134.

Through large scale data analysis, the quantification result 138 of the analysis may be obtained and stored. At the same time, when different applications are employed in the analysis of the same image, statistical discrepancies among the different applications may be generated. This may be used by the application result compensation generation unit 136 to generate corrections to the analysis result of each application. This may in turn be used to correct the analysis protocol specification 114.

Figure 2A:
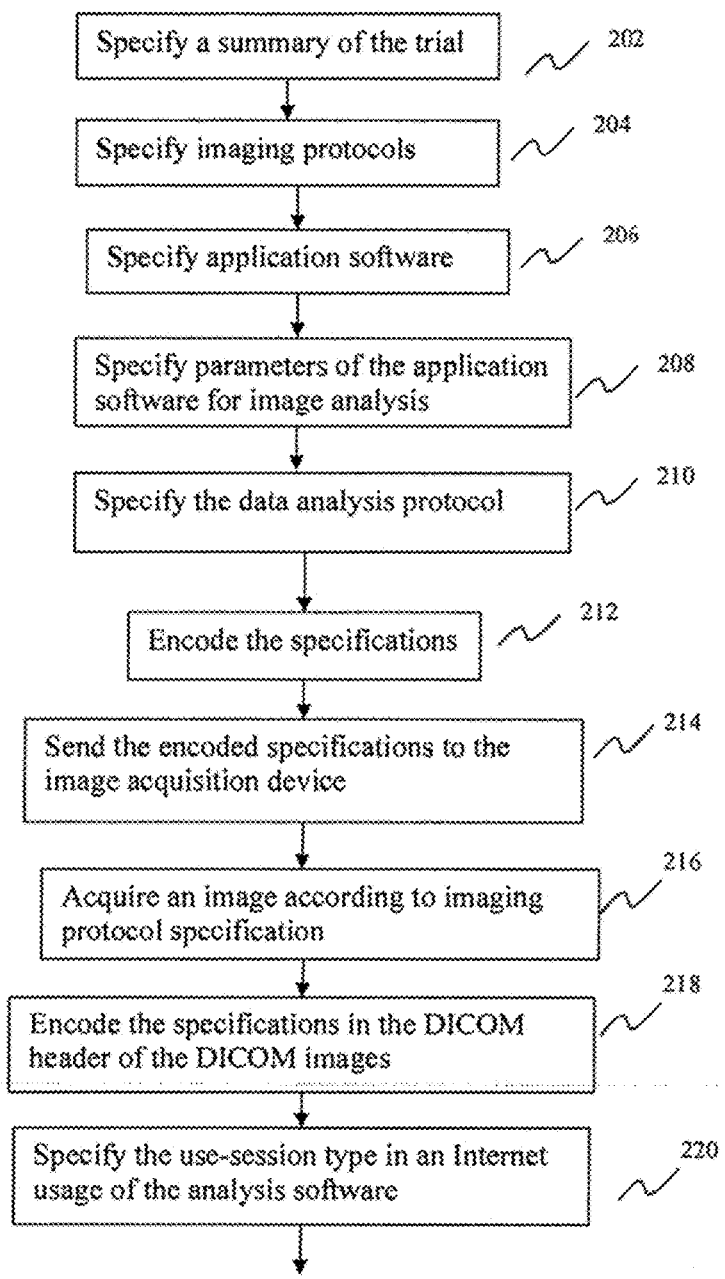
FIGS. 2a and 2b is a flow diagram for a platform for quantitative image analysis in accordance with an embodiment of the present disclosure.
Figure 2B:
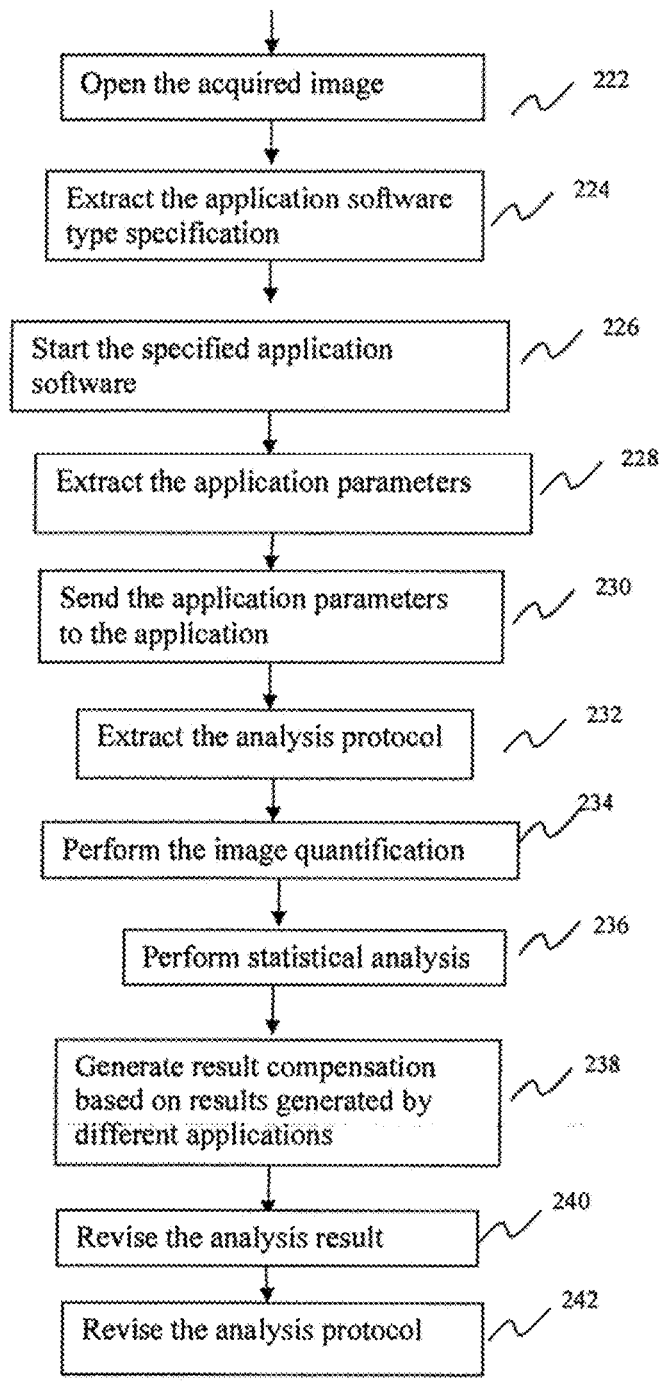

FIG. 2 shows a flow diagram of an embodiment of the system 100. At step 202, a summary of the trial is specified. This information may be displayed to a user when application software is used to analyze the clinical data. At step 204, the imaging protocols are specified. In an embodiment, this may include, but is not limited to, the imaging modality, the acquisition parameters of the imaging device, the contrast agent type, and the injection speed of the contrast agent. At step 206, the analysis software that needs to be used to analyze the images is specified. At step 208, critical analysis parameters, such as the Hounsfield unit that specifies the noise level in CT liver quantification, to be used by the analysis software are specified. At step 210, the analysis protocol is specified. In an embodiment, this may include, but is not limited to, the statistical method to be used, and the compensation of the analysis result that may need to be applied to an application.

At step 212, all of the above specifications are encoded for transmission. At step 212, the encoded specifications may also be sent to the image acquisition device directly or over a network. At step 216, the images are acquired according to the imaging protocol specifications. After the images are acquired, all the specifications are put into a designed DICOM tag of the resulting DICOM image. At step 220, when the user starts an analysis session, the user specifies whether the use-session is a single user or multi-user session. In an embodiment, if a multi-user session is specified, all the participating users may control the mouse and operations of the analysis software at the same time, independently or in parallel. Such collaborative use may be helpful when there is a need to consult other users for an opinion.

At step 222 an image is selected by the image-centered application dispatch unit 124. From the DICOM header information the application software type is extracted at step 224. At step 226, the specified application software is automatically started based on the extracted application type. At step 228, the application parameters are extracted from the DICOM header. The extracted application parameters are sent to the already started application at step 230. The application software then uses the pre-defined parameters in its internal analysis of the images. At step 234, the quantification of the image is performed to generate quantification results of the input image. After a large number of cases or images are analyzed, statistical analysis of the quantification result may be performed at step 236. At step 238, statistical discrepancies among different analysis applications may be collected and analyzed. The discrepancies may be applied to correct the analysis result at step 240. At step 242 the analysis protocol may be revised to incorporate any updates of the discrepancies used in the previous analysis protocol.

Figure 3:
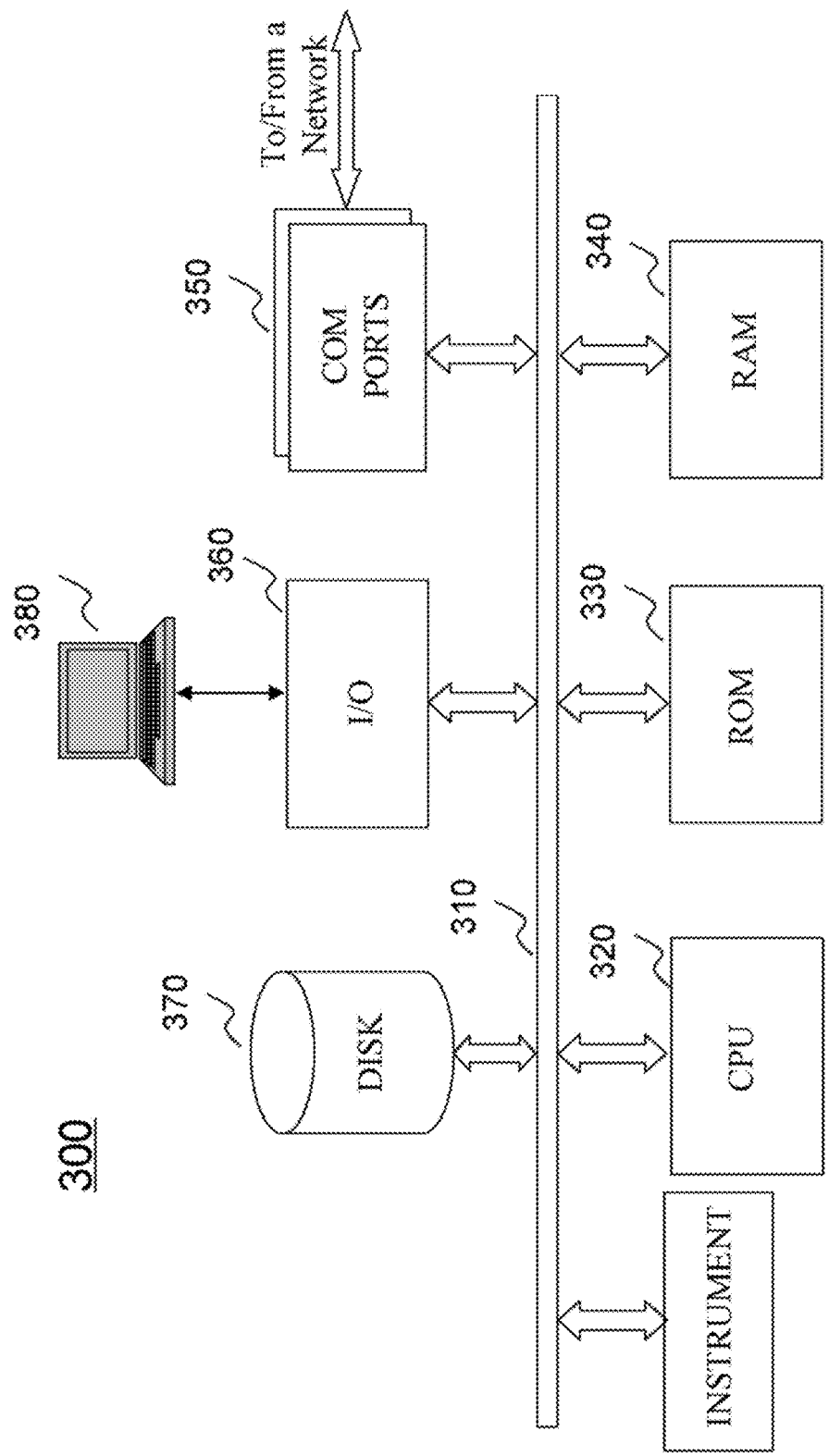
FIG. 3 depicts a computer system for carrying out the system and method of the present disclosure in accordance with the present disclosure.

FIG. 3 depicts a general computer architecture on which the present teaching can be implemented and has a functional block diagram illustration of a computer hardware platform which includes user interface elements. The computer may be a general purpose computer or a special purpose computer. This computer 300 can be used to implement any components of the image analysis platform as described herein. For example, the image display, image storing, image processing, image analysis, image acquisition unit, can all be implemented on a computer such as computer 300, via its hardware, software program, firmware, or a combination thereof. Although only one such computer is shown, for convenience, the computer functions relating to the disclosure described herein may be implemented in a distributed fashion on a number of similar platforms, to distribute the processing load.

The computer 300, for example, includes COM ports 350 connected to and from a network connected thereto to facilitate data communications. The computer 300 also includes a central processing unit (CPU) 320, in the form of one or more processors, for executing program instructions. The exemplary computer platform includes an internal communication bus 310, program storage and data storage of different forms, e.g., disk 370, read only memory (ROM) 330, or random access memory (RAM) 340, for various data files to be processed and/or communicated by the computer, as well as possibly program instructions to be executed by the CPU. The computer 300 also includes an I/O component 360, supporting input/output flows between the computer and other components therein such as user interface elements 380. The computer 300 may also receive programming and data via network communications.

Hence, aspects of the image analysis platform as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will recognize that the present teachings are amenable to a variety of modifications and/or enhancements. For example, although the implementation of various components described above may be embodied in a hardware device, it can also be implemented as a software only solution. In addition, the image analysis platform as disclosed herein can be implemented as a firmware, firmware/software combination, firmware/hardware combination, or a hardware/firmware/software combination While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A system having at least one processor, storage, and a communication platform connected to a network for analyzing an image, the system comprising:
    a trial specification unit, implemented on the at least one processor, configured to obtain one or more imaging protocols, each of which specifying how an image is to be acquired;
    an encoding unit, implemented on the at least one processor, configured to encode information related to clinical trial protocols including the one or more imaging protocols;
    the communication platform configured to
        transmit the encoded information related to clinical trial protocols, via the network, to an acquisition unit, so that the acquisition unit can acquire an image based, at least in part, on the one or more imaging protocols and append the encoded information related to clinical trial protocols to the acquired image, and
        receive the acquired image appended with the encoded information related to clinical trial protocols from the acquisition unit;
    an application dispatch unit, implemented on the at least one processor, configured to decode the appended information related to clinical trial protocols,
        identify a clinical trial protocol from the decoded information related to clinical trial protocols, and
        initialize a software application based on the identified clinical trial protocol;
    an analysis unit, implemented on the at least one processor, configured to perform an analysis of the received image utilizing the software application to obtain an analysis result; and
    an application result compensation generation unit, implemented on the at least one processor, configured to apply compensation data to the analysis result, wherein the compensation data is obtained from statistical analysis of prior use of the software application.

2. The system of claim 1, wherein the analysis result is used to generate clinical trial data.

3. The system of claim 1, wherein the compensation data is used by the software application to refine the analysis result.

4. The system of claim 1, wherein the information related to clinical trial protocols includes at least one of the following:
    a protocol description,
    an image type,
    an application type,
    an application parameter, and
    an analysis protocol.

5. The system of claim 4, wherein the encoded information is appended to a header of the image.

6. The system of claim 5, further comprising:
    an application repository configured to store a plurality of software applications for image processing; and
    a database for storing the received image, wherein the application dispatch unit is further configured to
        retrieve the image from the database, and
        select the software application from the plurality of software applications in the application repository to process the image.

7. The system of claim 6, wherein the selected software application generates results based on the analysis of the image and outputs the results to the analysis unit.

8. The system of claim 1, wherein the compensation data is used to revise the clinical trial protocols.

9. The system of claim 1, wherein the image includes a Digital Imaging and Communication in Medicine (DICOM) image.

10. A method implemented on a machine having at least one processor, storage, and a communication platform connected to a network for analyzing clinical trial data, the method comprising:
    obtaining one or more imaging protocols, each of which specifying how an image is to be acquired;
    encoding information related to clinical trial protocols including the one or more imaging protocols;
    transmitting the encoded information related to clinical trial protocols, via the network, to an acquisition unit, so that the acquisition unit acquires an image based, at least in part, on the one or more imaging protocols and appends the encoded information related to clinical trial protocols to the acquired image;
    receiving the image appended with the encoded information related to clinical trial protocols from the acquisition unit;
    decoding the appended information related to clinical trial protocols, via a dispatch unit;
    identifying a clinical trial protocol from the decoded information related to clinical trial protocols;
    initializing a software application based on the identified clinical trial protocol;
    performing an analysis of the received image utilizing the software application to obtain an analysis result; and
    applying compensation data to the analysis result, wherein the compensation data is obtained from statistical analysis of prior use of the software application.

11. The method of claim 10, wherein the compensation data is used by the software application to refine the analysis result.

12. The method of claim 10, wherein the compensation data is used to revise the clinical trial protocols.

13. The method of claim 10, wherein the analysis result is used to generate clinical trial data.

14. The method of claim 10, wherein the information related to clinical trial protocols includes at least one of the following:
    a protocol description,
    an image type,
    an application type,
    an application parameter, and
    an analysis protocol.

15. The method of claim 10, wherein the image includes a Digital Imaging and Communication in Medicine (DICOM) image.

16. A machine-readable tangible and non-transitory medium, having information recorded thereon for analyzing clinical trial data, wherein the information, when read by the machine, causes the machine to perform the following:
    obtaining one or more imaging protocols, each of which specifying how an image is to be acquired;
    encoding information related to clinical trial protocols including the one or more imaging protocols;
    transmitting the encoded information related to clinical trial protocols, via the network, to an acquisition unit, so that the acquisition unit acquires an image based, at least in part, on the one or more imaging protocols and appends the encoded information related to clinical trial protocols to the acquired image;

receiving the image appended with the encoded information related to clinical trial protocols from the acquisition unit;

decoding the appended information related to clinical trial protocols, via a dispatch unit;

identifying a clinical trial protocol from the decoded information related to clinical trial protocols;

initializing a software application based on the identified clinical trial protocol;

performing an analysis of the received image utilizing the software application to obtain an analysis result; and applying compensation data to the analysis result, wherein the compensation data is obtained from statistical analysis of prior use of the software application.

17. The medium of claim 16, wherein the compensation data is used by the software application to refine the analysis result.

18. The medium of claim 16, wherein the compensation data is used to revise the clinical trial protocols.

19. The medium of claim 16, wherein the analysis result is used to generate clinical trial data.

20. The medium of claim 16, wherein the information related to clinical trial protocols includes at least one of the following:
  a protocol description,
  an image type,
  an application type,
  an application parameter, and an analysis protocol.

21. The medium of claim 16, wherein the image includes a Digital Imaging and Communication in Medicine (DICOM) image.

* * * * *